(12) United States Patent
Klofta et al.

(10) Patent No.: US 6,904,865 B2
(45) Date of Patent: Jun. 14, 2005

(54) WETNESS INDICATOR HAVING IMPROVED COLORANT RETENTION AND DURABILITY

(75) Inventors: Thomas James Klofta, Cincinnati, OH (US); Brandon Ellis Wise, Cincinnati, OH (US); Donald Carroll Roe, West Chester, OH (US)

(73) Assignee: The Procter and Gamble Company, Cincinnati, OH (US)

(*) Notice: Subject to any disclaimer, the term of this patent is extended or adjusted under 35 U.S.C. 154(b) by 0 days.

(21) Appl. No.: 10/323,574

(22) Filed: Dec. 18, 2002

(65) Prior Publication Data

US 2003/0154904 A1 Aug. 21, 2003

Related U.S. Application Data

(63) Continuation-in-part of application No. 10/078,137, filed on Feb. 19, 2002, now Pat. No. 6,772,708.

(51) Int. Cl.[7] ............................................... A61F 13/42
(52) U.S. Cl. ....................... 116/206; 116/200; 604/361; 252/194
(58) Field of Search ................................ 116/206, 200; 252/194; 604/361, 385.01, 362

(56) References Cited

U.S. PATENT DOCUMENTS

| | | | |
|---|---|---|---|
| 2,681,032 A | 6/1954 | Shaw | |
| 3,607,782 A | * 9/1971 | Rosen | .................. 436/40 |
| 3,675,654 A | 7/1972 | Baker et al. | |
| 3,702,610 A | 11/1972 | Sheppard et al. | |
| 3,731,685 A | 5/1973 | Eidus | |
| 3,759,261 A | 9/1973 | Wang | |
| 3,918,454 A | 11/1975 | Korodi et al. | |
| 3,952,746 A | 4/1976 | Summers | |
| 4,022,211 A | 5/1977 | Timmons et al. | |
| 4,028,876 A | * 6/1977 | Delatorre | .................. 368/89 |
| 4,192,311 A | 3/1980 | Felfoldi | |
| 4,231,370 A | * 11/1980 | Mroz et al. | .................. 604/361 |
| 4,287,153 A | 9/1981 | Towsend | |
| 4,327,731 A | 5/1982 | Powell | |
| 4,507,121 A | 3/1985 | Leung | |
| 4,681,576 A | 7/1987 | Colon et al. | |
| 4,705,513 A | 11/1987 | Sheldon et al. | |
| 4,735,622 A | 4/1988 | Acuff et al. | |
| 4,738,674 A | 4/1988 | Todd et al. | |
| 4,743,238 A | 5/1988 | Colon et al. | |
| 4,834,733 A | 5/1989 | Huntoon et al. | |
| 4,895,567 A | 1/1990 | Colon et al. | |
| 4,931,051 A | 6/1990 | Castello | |
| 5,035,691 A | 7/1991 | Zimmel et al. | |
| 5,066,711 A | 11/1991 | Colon et al. | |
| 5,078,708 A | 1/1992 | Haque | |
| 5,085,918 A | * 2/1992 | Rajan et al. | ............. 428/195.1 |
| 5,089,548 A | 2/1992 | Zimmel et al. | |
| 5,167,652 A | 12/1992 | Mueller | |
| 5,183,742 A | 2/1993 | Omoto et al. | |
| 5,197,958 A | 3/1993 | Howell | |
| 5,342,861 A | 8/1994 | Raykovitz | |
| 5,354,289 A | 10/1994 | Mitchell et al. | |
| H1376 H | 11/1994 | Osborn, III et al. | |
| 5,389,093 A | 2/1995 | Howell | |
| 5,435,010 A | * 7/1995 | May | .................. 2/67 |
| 5,468,236 A | 11/1995 | Everhart et al. | |
| 5,647,863 A | 7/1997 | Hammons et al. | |
| 5,690,624 A | * 11/1997 | Sasaki et al. | ............... 604/361 |
| 5,766,212 A | 6/1998 | Jitoe et al. | |
| 5,834,099 A | 11/1998 | Steinhardt et al. | |
| 5,902,296 A | 5/1999 | Fluyeras | |
| 5,902,669 A | 5/1999 | Steinhardt et al. | |
| 5,947,943 A | 9/1999 | Lee | |
| 6,066,774 A | 5/2000 | Roe | |
| 6,075,178 A | 6/2000 | La Wilhelm et al. | |
| 6,168,655 B1 | * 1/2001 | Nohr et al. | ............... 106/31.58 |
| 6,297,424 B1 | 10/2001 | Olson et al. | |
| 6,320,096 B1 | * 11/2001 | Inoue et al. | ................ 604/378 |
| 6,452,873 B1 | * 9/2002 | Holt et al. | .................. 368/327 |
| 6,464,635 B1 | * 10/2002 | Jimenez Cerrato et al. | . 600/362 |
| 6,501,002 B1 | * 12/2002 | Roe et al. | .................. 604/362 |
| 6,515,194 B2 | * 2/2003 | Neading et al. | ............. 604/361 |
| 6,710,221 B1 | * 3/2004 | Pierce et al. | ................ 604/361 |
| 6,747,185 B2 | * 6/2004 | Inoue et al. | ................ 604/361 |
| 6,772,708 B2 | * 8/2004 | Klofta et al. | ............... 116/206 |
| 2002/0137417 A1 | * 9/2002 | Tebbe | ........................ 442/130 |
| 2003/0114822 A1 | * 6/2003 | Collando et al. | ...... 604/385.01 |

FOREIGN PATENT DOCUMENTS

| | | |
|---|---|---|
| EP | 0 203 715 A2 | 12/1986 |
| EP | 0 776 645 A1 | 6/1997 |
| EP | 0 925 769 A2 | 6/1999 |
| EP | 1 034 758 A1 | 9/2000 |
| EP | 1 023 024 B1 | 4/2002 |
| WO | WO 95/00099 A1 | 1/1995 |
| WO | WO 98/04225 A1 | 2/1998 |
| WO | WO 99/02985 A1 | 1/1999 |
| WO | WO 99/20216 | 4/1999 |
| WO | WO 99/56690 A1 | 11/1999 |
| WO | WO 00/00233 A1 | 1/2000 |
| WO | WO 00/15169 A1 | 3/2000 |
| WO | WO 00/76438 A2 | 12/2000 |
| WO | WO 00/76439 A2 | 12/2000 |
| WO | WO 00/76442 A1 | 12/2000 |
| WO | WO 00/76443 A1 | 12/2000 |

* cited by examiner

Primary Examiner—Christopher W. Fulton
Assistant Examiner—Amy R. Cohen
(74) Attorney, Agent, or Firm—Eric T. Addington; Dara M. Kendall; Ken K. Patel

(57) ABSTRACT

Wetness indicating compositions having improved colorant retention and durability and to wearable articles comprising this wetness indicating composition are provided.

19 Claims, No Drawings

WETNESS INDICATOR HAVING IMPROVED COLORANT RETENTION AND DURABILITY

CROSS REFERENCE TO RELATED APPLICATIONS

This application is a continuation-in-part of patent application Ser. No. 10/078,137, filed Feb. 19, 2002 now U.S. Pat. No. 6,772,708.

FIELD OF THE INVENTION

This invention is directed to a wetness indicating composition having both improved colorant retention and durability and to wearable articles comprising this wetness indicating composition.

BACKGROUND OF THE INVENTION

Many advances have been made since the introduction of the disposable absorbent article including the introduction of wetness indicating compositions. Such compositions may comprise a colorant adapted to change in appearance, i.e., appear, disappear, change color, etc., upon contact with liquid, such as, urine, menses, in the article. Certain attempts have been made to retain the colorant, such as, incorporating the colorant into adhesive compositions having high melting temperatures.

However, there are problems associated with existing wetness indicating compositions. One problem of most, if not all, existing wetness indicating compositions is poor retention of the colorant within the composition upon contact with liquid. That is, the colorant diffuses out of, i.e., leaches from, the composition and migrates toward and possibly through portions of the absorbent article on which it is contained, e.g. the backsheet and/or topsheet of a disposable absorbent article and ultimately onto the wearer. This may lead to consumer negatives, such as, clothing or bedding staining, and/or may cause the wetness indicator to appear unsightly through the backsheet. For example, the applied pattern of the wetness indicator composition may become blurry, indistinct, or otherwise aesthetically displeasing.

Another problem is premature activation in high humidity environments, which may render the wetness indicator less effective in detecting and/or indicating the presence of liquid. For instance, exposure to a high level of humidity may partially activate wetness indicating compositions that are not highly resistant to colorant leaching and thereby make any color change in the presence of liquid less noticeable.

Finally, any wetness indicating composition attached to a substrate, such as, the backsheet of a disposable absorbent article, needs to have sufficient wet and dry cohesion and/or flexibility to be fully retained on the substrate. The normal bending, flexing and/or folding associated with the use of the substrate, such as, being worn in the case of a disposable absorbent article, puts stresses on the wetness indicating composition, possibly leading to portions of the wetness indicating composition to chip off the substrate on to which it is applied.

However, the need remains for a wetness indicating composition that is highly resistant to colorant leaching, as described above, and is resistant to premature activation in high humidity environments. Furthermore, the any wetness indicating composition attached to a substrate needs to have sufficient wet and dry cohesion and/or flexibility to be fully retained on a substrate.

SUMMARY OF THE INVENTION

A first aspect of the present invention provides, a wetness indicating composition comprising:

(a) a colorant, the colorant having an initial color state, the initial color state being associated with a first state of the composition and a final color state, the final color state being associated with a second state of the composition; and (b) a matrix comprising a mixture of a first binding agent and a second binding agent; wherein the first binding agent immobilizing the colorant when it is in its said initial color state and the second binding agent immobilizing the colorant when it is in its said final color state.

A second aspect of the present invention provides, a disposable absorbent article comprising a wetness indicating composition affixed to a structural component of the article, the wetness indicating composition comprising:

(a) a colorant, the colorant having an initial color state, the initial color state being associated with a first state of the composition and a final color state, the final color state being associated with a second state of the composition; and (b) a matrix comprising a mixture of a first binding agent and a second binding agent; wherein the first binding agent immobilizing the colorant when it is in its said initial color state and the second binding agent immobilizing the colorant when it is in its said final color state and the ratio of the first binding agent to the second binding agent is from about 2:1 to about 40:1.

All documents cited are, in relevant part, incorporated herein by reference; the citation of any document is not to be construed as an admission that it is prior art with respect to the present invention.

It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein.

All percentages, ratios and proportions are by weight, and all temperatures are in degrees Celsius (° C.), unless otherwise specified. All measurements are in SI units unless otherwise specified.

DETAILED DESCRIPTION OF THE INVENTION

Wetness Indicator Composition

The wetness indicator compositions of the present invention comprise a colorant, a matrix, and optional additional ingredients, all of which are illustrated in more detail herein. Furthermore, the wetness indicator compositions of the present invention may optionally be attached to a substrate, such as, a structural component of a absorbent article. Substrates, disposable absorbent articles and structural components thereof are illustrated in more detail herein.

(a) Colorant

The wetness indicator compositions of the present invention comprise a colorant. The colorant has an initial color state, which is associated with a first state of the wetness indicator composition. Examples of this first color state include, but are not limited to, colors visible to the human eye, such as, red, blue, green, indigo, violet, yellow, orange, purple, and the like; colors not visible to the human eye, such as, colors visible in the ultra violet (or UV), or infra red (or IR) portion of the electromagnetic spectrum, and the like. The first color state may be translucent or opaque. The colorant also has a final color state, which is associated with a second state of the wetness indicator composition. Examples of this second color state include, but are not limited to, colors visible to the human eye, such as, red, blue, green, indigo, violet, yellow, orange, purple, and the like; colors not visible to the human eye, such as, colors visible in the UV, or IR portion of the electromagnetic spectrum, and the like. The second color state may be translucent, opaque, or have a change in intensity or visual distinctiveness, and the like, when compared to the first color state. The initial color state of the colorant is different, in some form, to the final color state. For example, the initial color state may be a first color, such as, red, while the second color state may be a different color, such as blue; or the initial color state may be a first color, such as, red, while the second color state may be transparent, such as, a color not visible to the human eye,.and only visible in the UV portion of the electromagnetic spectrum.

In the wetness indicator compositions of the present invention, the initial color state is associated with a first state of the wetness indicator composition. This first state of the wetness indicator composition includes, but is not limited to: a specific pH or pH range; absence or presence of a specific compound or compounds, such as, water, urea, dissolved oxygen, ions, such as, but not limited to, iron, calcium, sodium, chloride and combinations thereof, sugars, such as, glucose, enzymes; and combinations thereof; microbiological flora and fauna, such as, bacteria and the like; some threshold level of a compound or composition, such as, water, urine etc., below a certain amount; and combinations thereof.

In the wetness indicator compositions of the present invention the final color state is associated with a second state of the wetness indicator composition. This second state of the wetness indicator composition includes, but is not limited to: a specific pH or pH range; absence or presence of a specific compound or compounds, such as, water, urea, dissolved oxygen, ions, such as, but not limited to, iron, calcium, sodium, chloride and combinations thereof, sugars, such as, glucose, enzymes; and combinations thereof; microbiological flora and fauna, such as, bacteria and the like; some threshold level of a compound or composition, such as, water, urine, menses, blood and the like; and combinations thereof.

In one embodiment of the present invention the first state is a specific pH or pH range and the second state is a specific pH or pH range different to the specific pH or pH range of the first state. In one optional embodiment of the present invention the second state is the pH or pH range of urine, preferably human urine, as measured as a neat solution at human body temperature (typically 37.6° C.). The pH or pH range of urine is typically about 5.5 to about 8.0. In this optional embodiment, the first state may be a specific pH or pH range which is more acidic or more basic than the second state, that is, a pH of less than about 5.5 or greater than about 8.0. In one optional embodiment of the present invention, the colorant is a pH indicator. Non-limiting examples of suitable pH indicators include: sulfonephthalein pH indicators, such as, bromocresol green, m-cresol purple, cresol red, chlorophenol red, bromothymol blue, bromopyrogallol red, bromoxylenol blue, and bromophenol blue; monoazo dyes, such as, acid alizarin violet N; monoazo pyrazoline dyes, such as, acid yellow 34; diazo dyes, such as, acid black 24; acid anthraquinone dyes, such as, acid black 48; amphoteric anthraquinone dyes, such as, acid blue 45; triphenylmethane dyes, such as, acid fuchsin; phthalein type dyes, such as, o-cresolphthalein; xanthene dyes, such as, 2',7'-dichlorofluorescein eosin B; heterocyclic acridine aromatics, such as, acridine orange; diphenylmethane dyes, such as, auramine O; triphenylmethane dyes, such as, basic fuchsin; cationic thiazine dyes, such as, azure C; cationic anthraquinone dyes, such as, basic blue 47; phthalocyanine type dyes, such as, copper phthalocyanine; quaternized phthalocyanine type dyes, such as, alcec blue; cationic polymethine dyes, such as, astrazon orange G; anthraquinone type, such as, alizarin; the neutral complex dyes, such as, azure A eosinate; the terpene type dyes, such as, trans-beta-carotene; and combinations thereof.

In one optional embodiment of the present invention, the colorant is a sulfonephthalein pH indicator, such as, but not limited to, bromocresol green, m-cresol purple, cresol red, chlorophenol red, bromothymol blue, bromopyrogallol red, bromoxylenol blue, bromophenol blue, and combinations thereof. In an acidic state, the sulfonephthalein class of indicators have a "neutral" charge and are typically yellow in color. The neutral charge enhances the solubility of these pH indicators in the first binding agent, as described herein. Upon contact with liquid, such as urine, having a pH higher than their $pK_a$, the sulfonephthalein class of pH indicators typically change to a blue-green color.

In another optional embodiment of the present invention the wetness indicator composition may comprise of two or more colorants, each having at least one of their first and second state different, i.e., different $pK_a$ values, a pH and an enzyme trigger, etc., colors, or other properties. The varying first and second states may facilitate interactive scenes, sequences, or displays providing information regarding relative fullness/wetness of the article or merely provide entertainment and/or aesthetic value. For example, the wetness indicating composition may contain one colorant that turns blue and another that turns red upon contact with urine. Alternatively, one portion of the graphic may appear and another portion may disappear upon contact with liquid, such as urine, menses, blood, and the like.

In another optional embodiment of the present invention the wetness indicator composition may comprise two or more colorants, each having their first and second state the same.

The colorant is typically employed in compositions at levels which are effective at indicating the presence of a liquid, preferably from about 0.001% to about 5%, more preferably from about 0.005% to about 2%, and even more preferably still from about 0.01% to about 1%, by weight of the composition.

(b) Matrix

The compositions of the present invention comprise a matrix comprising first and second binding agents, both of which are illustrated in more detail herein. The matrix acts to hold the colorant in place before, during and after contact with liquid. The matrix of the present invention is preferably highly resistant to colorant leaching, and is preferably resistant to premature activation in high humidity environments. Upon contact with liquid, such as urine, menses, blood or the like, the matrix allows sufficient liquid to contact the colorant and effect a change in appearance. The matrix concurrently prevents the colorant, in either its initial color state or final color state, from leaching out of the matrix into the surrounding environment, such as, the absorbent core of a disposable absorbent article.

The leaching inhibition is particularly beneficial in locking the colorant within the matrix on a substrate, such as the backsheet of a disposable absorbent article, rather than allowing free diffusion of the colorant through the various parts of the disposable absorbent article, such as, the absorbent core, topsheet etc. In addition, a clearer and more distinct wetness indicator pattern may be produced wherein colorants are locked into the matrix. As noted, colorants that diffuse out of the wetness indicator pattern tend to appear blurred and less distinct.

Furthermore, when the wetness indicating composition is attached to a substrate, the matrix and consequently the composition, should have sufficient wet and dry cohesion and/or flexibility to remain fully retained on the substrate. In other words, the composition retains sufficient flexibility and cohesion to prevent portions of the composition from separating, such as, portions of the composition chipping off or flaking off from the rest of the composition and/or the substrate.

The matrix, including both the first and second binding agents is typically employed in compositions at levels which are effective at immobilizing the colorant, preferably from about 5% to about 95%, more preferably from about 10% to about 80%, and even more preferably still from about 25% to about 75%, by weight of the composition.

(i) First Binding Agent

The first binding agent may be any material which immobilizes the colorant when the colorant is in its initial color state. There are various materials which may be suitable for use as the first binding agent for the wetness indicating compositions of the present invention. The material selected as the first binding agent will be any material which immobilizes the colorant when in its first color state. In one embodiment of the present invention, possible first binding agents include, but are not limited to, rosin esters, polymerized rosins, styrenated terpenes, polyterpene resins, terpene phenolics, and combinations thereof.

In one optional embodiment of the present invention, the first binding agent is a rosin ester. Rosin ester, also known as ester gum, is the "compound" obtained by the esterification of rosin, with a polyhydric alcohol, such as, glycerol. Rosin is the resin left after distilling turpentine from the exudation of a species of pine, e.g. *Pinus palustris*. One suitable rosin ester is Sylvatac RE99-70 available from Arizona Chemical Incorporated (Jacksonville, Fla.).

In addition to being suitable first binding agent, rosin esters may also be an effective solvent for some of the other optional ingredients in these wetness indicating compositions. Furthermore, while not wishing to be limited by theory, rosin esters acidity is believed to contribute to the preservation of particular colorants, such as, but not limited to, pH indicators.

The first binding material immobilizes the colorant when in its initial color state. How the first binding material immobilizes to the colorant when in its initial color state depends upon both what the first binding material and colorant are. For example, if the colorant where in its initial color state an uncharged long chain molecule and the first binding material another uncharged long chain molecule then the bond formed may be, for example, a covalent bond, hydrogen bonds or the like. Another example, if the colorant where in its initial color state a molecule having a overall zero charge, such as a zwitterions, and the first binding material an uncharged long chain molecule then the bond formed may be, for example, a covalent bond, hydrogen bond, polar covalent bond or the like.

In one embodiment of the present invention the first binding agent immobilizes the colorant when the colorant is in its initial color state by one or more forces selected from the group consisting of adhesion, hydrogen bonding, polar covalent bonding, Van der Waals forces, dipole-dipole forces, London dispersion forces and combinations thereof.

The first binding agent is typically employed in compositions at levels which are effective at immobilizing the colorant in its first state, preferably from about 4% to about 90%, more preferably from about 10% to about 75%, and even more preferably still from about 20% to about 65%, by weight of the composition.

(ii) Second Binding Agent

The second binding agent may be any material which immobilizes the colorant when the colorant is in its final color state. There are various materials which may be suitable for use as the second binding agent for the wetness indicating compositions of the present invention.

In one embodiment of the present invention the second binding agents may be selected from, but are not limited to: quaternary ammonium compounds, such as but not limited to, ethoxylated quaternary ammonium compounds, alkyltrimethylammonium compounds, dialkydimethylammonium quaternary compounds and the like; amine acid salts; polyacryamidopropyltrimmonium chloride; betaines, such as but not limited to, alkyl betaines, alkyl amido betaines, imidazolinium betaines; quaternized poly(vinylpyridine); amidoamine acid salts; poly(imine) acid salts; polyethylene imine acid salts; cationic polyacryamides; poly(vinylamine) acid salts; cationic ionene polymers; poly (vinylimidazolinium salts); quaternized silicone compounds, such as but not limited to, the diquaternary polydimethylsiloxanes; poly(vinyl alcohol) quaternary materials; cationic guars; polydimethyldiallylammonium chloride; cationic exchange resins; anionic exchange resins; copolymers of vinylpyrrolidone and methyacrylamidopropyltrimethylammonium chloride; acidified polyvinylpolypyrrolidones; acidified copolymers of vinylpyrrolidone and vinylacetate; acidified copolymers of vinylpyrrolidone and dimethylaminoethylmetacrylate; copolymers of vinylpyrrolidone and methacrylamidopropyl trimethlyammonium chloride; copolymers of quaternized vinylpyrrolidone and dimethylaminoethylmethacrylate; acidified copolymers of vinylpyrrolidone and styrene; acidified copolymers of vinylpyrrolidone and acrylic acid; cationic polyelectrolyte polymers; cationic clay, such as but not limited to, sodium montmorillonite, vermiculite, kaolinite; clays reacted with quaternary compounds, such as, tetramethylammonium chloride; polyquarternized amines; acidified n-alkyl-2-pyrrolidones; polyacrylic acid polymers; $C_8$ $C_{24}$ organic acids, such as but not limited to, stearic acid; and combinations thereof.

In one optional embodiment of the present invention the second binding agent is selected from the group consisting of quaternary ammonium compounds, cationic clay, polyacrylic acid polymers, organic acids, and combinations thereof. Examples of suitable quaternary ammonium compounds include, but are not limited to, dimethyl(2-ethylhexylhydrogenatedtallowalkyl) ammonium methyl sulfate, cocoalkylmethyl[ethoxylated(15)] ammonium chloride, dodecyltrimethyl ammonium chloride, hexadecyltrimethyl ammonium methyl sulfate, octadecyltrimethyl ammonium chloride, dicocoalkyldimethly ammonium chloride, di(hydrogenated tallowalkyl)dimethyl ammonium chloride, and distearyldimethyl ammonium chloride.

One suitable quaternary ammonium compound is dimethyl(2-ethylhexylhydrogenatedtallowalkyl) ammonium methyl sulfate which is available from Akzo Incorporated, Chicago, Ill. as HTL8(W)-MS. Another suitable quaternary ammonium compound is cocoalkylmethyl[ethoxylated(15)] ammonium chloride, which is also available from Akzo Incorporated, Chicago, Ill. as Ethoquad C/25.

It should be noted that the counter anion associated with the quaternary compound, or any second binding agent having one or more cationic group, is not specifically limited to chloride. Other anions can also be employed and non-limiting examples include methyl sulfate and nitrite. Similarly, any suitable counter cation, such as, but not limited to, sodium, potassium, calcium, ammonium, substituted ammonium and the like, may be associated with a second binding agent having one or more anionic group.

The second binding material immobilizes the colorant when in its final color state. How the second binding material immobilizes the colorant when in its final color state depends upon the chemical composition of both the second binding material and colorant. For example, if the colorant's final color state is that of an anionic long chain molecule and the second binding material is a cationic molecule, then the bond formed may be, for example, an ionic bond, a covalent bond, or the like. Another example, if the colorant's final color state is that of a cationic molecule, and the second binding material is an anionic long chain molecule, then the bond formed may be, for example, an ionic bond, covalent bond, or the like.

In one embodiment of the present invention the second binding agent immobilizes the colorant when the colorant is in its final color state by one or more selected from the group consisting of covalent bonding, ionic bonding and combinations thereof.

Without wishing to be bound by theory, it is believed that when the colorant is an anion in its final color state and the second binding agent is a cation or the colorant is a cation in its final color state and the second binding agent is an anion, the second binding agent forms an ionically bonded coacervate with the colorant. For example, when the final state associated with a colorant's final color state is the pH of urine, contacting the colorant with urine will change the colorant to its final color state, i.e. an anion, and this forms an ionic bond with the second binding agent, which is a cation. The coacervate formation is due to the strong coulombic interaction between the opposite charges of the colorant and the second binding agent. The coacervate complex formed between the colorant and the second binding agent neutralizes the charge in both species and dramatically reduces both of their solubilities in polar solvents such as water or urine, thereby dramatically inhibiting leaching of the colorant from the matrix. Also, since the charges on both the cationic and anionic species are neutralized through this coacervate formation, the coacervate complex is more hydrophobic in nature. This hydrophobicity of the coacervate leads to increased intermolecular forces between the coacervate and components of the matrix. These intermolecular forces may further limit the diffusion and mobility of the colorant into an aqueous environment such as urine.

In certain optional embodiments of the present invention, use of cationic quaternary ammonium compounds as the second binding agent may also function to darken or intensify the color change of certain colorants, especially those belonging to the sulfonephthalein class of pH indicators. Without wishing to be bound by theory, it is believed this darkening is due to several possible factors: 1) alkaline impurities within the quaternary ammonium raw material, 2) absorption shifting and absorptivity coefficient increases due to coacervate formation and/or 3) increased formation of the colorant in its final color state.

The second binding agent is typically employed in compositions at levels which are effective at immobilizing the colorant in its second state, preferably from about 0.5% to about 20%, more preferably from about 0.5% to about 15%, and even more preferably still from about 0.5% to about 10%, by weight of the composition.

Ratio of First Binding Agent to Second Binding Agent

In one optional embodiment of the present invention the ratio of the first binding agent to second binding agent is preferably from about 2:1 to about 40:1, more preferably from about 5:1 to about 25:1 even more preferably from about 8:1 to about 20:1.

Optional Additional Ingredients

In one optional embodiment of the present invention, the wetness indicator composition may include optional ingredients, including, but not limited to, stabilizers, surfactants, structural adjuncts and combinations thereof.

The optional additional ingredients, when present, are typically employed in compositions at levels which are effective at providing the benefits of the optional additional ingredient or ingredients, preferably from about 0.001% to about 50%, more preferably from about 0.1% to about 40%, and even more preferably still from about 1% to about 35%, by weight of the composition.

(c) Stabilizer

In one optional embodiment of the present invention the wetness indicator composition of the present invention may include a stabilizer. It is especially preferred to include a stabilizer when the colorant is a pH indicator.

In one embodiment of the present invention, the optional stabilizer is an acidic stabilizer. In another embodiment of the present invention, the optional stabilizer is a basic stabilizer.

The inclusion of a stabilizer, while not wishing to be limited by theory, is believed to play a role in stabilizing the colorant against premature changes caused by exposure to humid environments, by maintaining a stable pH, such as a low pH environment with an acidic stabilizer, around the colorant even when the system is exposed to high humidities. This maintenance of a stable pH environment keeps the colorant, especially when the colorant is a pH indicator, in its initial color state. Acidic stabilizers which are particularly effective in stabilizing the wetness indicator formula to high humidities include, but are not limited to: organic acids, such as, but not limited to, fatty acids such as stearic acid, palmitic acid, fruit acids e.g., citric acid, and salicylic acid; esters, such as, citrate esters, e.g., monostearyl citrate, glycolate esters, lactate esters; phosphorus containing organic acids, such as, monostearyl phosphate; ether carboxylic acids; N-acyl sarcosinic acids; N-acyl glutamic acids; N-acyl ethylenediaminetriacetic acid; alkane sulfonic acids; alpha-olefin sulfonic acids; alpha-sulfonic acid fatty acid methyl esters; sulfate esters; inorganic acids, such as, phosphoric acid; and combinations thereof. Examples of suitable basic stabilizers include, but are not limited to: monoethanolamine; diethanolamine; triethanolamine; dipropylenetriamine; diiosopropyl amine; organic diamines, such as, but not limited to, 1,3-bis(methylamine)-cyclohexane, 1,3-pentanediamine; inorganic bases, such as, but not limited to, sodium hydroxide, magnesium hydroxide, and combinations thereof.

The stabilizer, when present is typically employed in compositions at levels which are effective at stabilizing the colorant, preferably from about 0.001% to about 30%, more preferably from about 0.1% to about 20%, and even more preferably still from about 1% to about 15%, by weight of the composition.

(d) Surfactant

In one optional embodiment of the present invention the wetness indicator composition comprises a surfactant. The optional surfactant, while not wishing to be limited by theory, is believed to provide or enhance both composition phase stability and wettability, and also increase the speed of the change of the colorant from its initial color state to its final color state on contact with a liquid, such as urine. Suitable, but non-limiting examples of surfactants, include, but are not limited to, anionic surfactants, cationic surfactants and non-ionic surfactants. Non-limiting examples of suitable surfactants include, ethoxylated alcohols; alkoxylated alkylates such as, but not limited to, PEG-20 stearate; end group-capped alkoxylated alcohols; alkoxylated glyceryl; polyglyceryl alkylates such as, but not limited to, PEG-30 glyceryl stearate; glyceryl alkylates, such as, but not limited to, glyceryl stearate; alkoxylated hydrogenated castor oil; sterol derived surfactants, such as, but not limited to, alkoxylated lanolin, hydrogenated lanolin; alkoxylated sorbitan alkylates; sugar derived surfactants, such as, but not limited to, alkyl glycosides and sugar esters; poloxamers; polysorbates; sulfo succinic acid alkyl esters and combinations thereof.

While not wishing to be limited by theory, when the wetness indicator composition is applied to a substrate, the surfactant is believed to improve adhesion by reducing the contact angle of the wetness indicator composition on the substrate. The reduced contact angle leads to enhanced wetting such that the wetness indicator composition can more effectively coat the substrate.

The optional surfactant, when present, is typically employed in compositions at levels which are a surface effective amount, preferably from about 0.1% to about 30%, more preferably from about 1% to about 25%, and even more preferably still from about 5% to about 25%, by weight of the composition.

(e) Structural Adjunct

In one optional embodiment of the present invention, the wetness indicator composition may optionally comprise an optional structural adjunct. The optional structural adjunct may include, but is not limited to, HLB modifiers, viscosity modifiers, additional bonding agents, hardening agents, colorant solubilizers, other optional adjuncts and combinations thereof.

The optional structural adjunct, when present, is typically employed in compositions at levels which are a structurally effective amount, preferably from about 0.001% to about 50%, more preferably from about 0.1% to about 40%, and even more preferably still from about 1% to about 35%, by weight of the composition.

(i) Optional HLB Modifiers

In one optional embodiment of the present invention the wetness indicator composition may optionally comprise a HLB modifier. A HLB (Hydrophilic Lipophilic Balance) modifier changes the HLB ratio of a wetness indicator composition. HLB modifiers are typically added to the wetness indicator compositions of the present invention to increase the hydrophobicity of the wetness indicator composition as well as modifying the melting point of the wetness indicating composition, increase the flexibility of the wetness indicator composition, enhance the adhesion of the wetness indicator composition to any substrate, affect the leaching of the colorant, and/or alter the humidity resistance of the wetness indicator composition. Non-limiting examples of suitable HLB modifiers include, but are not limited to, natural and synthetic waxes including highly branched waxes, such as microcrystalline waxes, paraffin waxes, polyethylene waxes, polyethylene glycol type waxes, silicone waxes, beeswax, ozokerite, ceresin, carnauba wax and combinations thereof.

The HLB modifiers, when present, are typically employed in compositions at levels which are effective modifying the HLB of the wetness indicator composition, preferably from about 0.1% to about 40%, more preferably from about 1.0% to about 30%, and even more preferably still from about 1.0% to about 25%, by weight of the composition.

(ii) Optional Viscosity Modifiers

In one optional embodiment of the present invention, the wetness indicator composition may optionally comprise a viscosity modifier. While not wishing to be limited to theory, these viscosity modifiers are believed to contribute to increasing the flexibility and adhesion of the final wetness indicator formula. Suitable viscosity modifiers, include, but are not limited to: polymeric thickeners, such as, but not limited to, block copolymers having polystyrene blocks on both ends of a rubber molecule; copolymers of ethylene and vinyl acetate; hydrogenated castor oil polymers; metal salts of fatty acids; silicas and/or derivatized silicas; organoclays, such as, but not limited to, the modified and unmodified hectorites and bentonites, modified clays, such as, but not limited to, modified laponite clays, dibenzylidene sorbitol; alkyl galactomannan; aluminum magnesium hydroxide stearate/oil blends; lauroyl glutamic dibutylamide; and combinations thereof.

In one optional embodiment of the present invention, the viscosity modifier is ethylene-vinyl acetate (EVA) copolymer resins, such as, the Elvax brand of EVA's from DuPont Incorporated (Wilmington, Del.).

The optional viscosity modifiers, when present, are typically employed in compositions at levels which are effective at modifying the viscosity of the wetness indicator composition, preferably from about 0.01% to about 15%, more preferably from about 0.1% to about 10%, and even more preferably still from about 1.0% to about 10%, by weight of the composition.

(iii) Optional Hardening Agents

In one optional embodiment of the present invention, the wetness indicator compositions may optionally include a hardening agent. Illustrative, but non-limiting, examples of suitable hardening agents include, $C_{14}$–$C_{22}$ fatty alcohols, $C_{23}$–$C_{60}$ alcohols, $C_{14}$-$C_{22}$ fatty acids, $C_{23}$–$C_{60}$ carboxylic acids, hydrogenated vegetable oils, polymers, sorbitan esters, other high molecular weight esters (other than rosin esters), and combinations thereof.

The optional hardening agents, when present are typically employed in compositions at levels which are effective at hardening the wetness indicator composition, preferably from about 1% to about 50%, more preferably from about 1% to about 30%, and even more preferably still from about 1% to about 20% by weight of the composition.

(iv) Other Optional Adjuncts

The wetness indicator compositions of the present invention may optionally comprise other optional adjunct ingredients. Illustrative, but non-limiting example of such optional adjunct ingredients include: process aids; preservatives; additional bonding agents; colorant solubilizers; color modifying agents, such as, D&C Green #6, D&C Red #17, D&C Violet #2, D&C Yellow #11, and the like; chelants; anti-oxidants; solvents, such as, water, alcohols, polyols, such as, propylene glycol, and the like; and combinations thereof.

The other optional ingredients, when present are typically employed in compositions at levels which are effective at providing the benefits of the optional adjunct ingredients or ingredients, preferably from about 0.001% to about 5%, more preferably from about 0.002% to about 2%, and even more preferably still from about 0.003% to about 1%, by weight of the composition.

(f) Combinations of (c), (d) and (e).

In one optional embodiment of the present invention the wetness indicator compositions may comprise a combination of any one of optional ingredients (c), (d) and (e), all of which are illustrated in more detail herein.

Substrate

In one embodiment of the present invention, the wetness indicator composition of the present invention may be on and/or in a substrate. When present on a substrate, the wetness indicator composition will typically be placed on and/or in a substrate where the substrate will be contacted by a liquid, such as water, urine, menses, blood and the like. The substrate may include, but is not limited to, woven fabrics, nonwoven fabrics, films, sponges, and combinations thereof. The substrate may comprise synthetic and/or natural materials. In one embodiment of the present invention the optional substrate may be an article in its own right, such as, a continuous nonwoven fabric. In another embodiment of the present invention the substrate to which the wetness indicator may be applied or otherwise affixed comprises any one, or a combination of, structural components of an absorbent article, including, but not limited to, the backsheet, topsheet, fasteners, absorbent material, etc., or may be a separate element added or applied to the product. In one optional embodiment of the present invention the wetness indicator composition is applied to the absorbent article as a whole.

The manufacture of substrates, absorbent articles and structural components thereof, for use herein form no part of this invention. The following discussion is for convenience of formulation, but is not intended to limit the type of substrate used herein.

As used herein, the term "absorbent article" ("absorbent articles") refers to devices which absorb and contain body exudates and, more specifically, refers to devices which are placed against or in proximity to the body of the wearer to absorb and contain the various exudates, including but not limited to urine, menses, blood and the like, discharged from the body. Non-limiting examples of absorbent articles includes, bandages, adhesive bandages, wound dressings, cloth diapers, disposable absorbent articles, such as, disposable diapers, tampons, panty liners, feminine hygiene pads and the like. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). As used herein, the term "diaper" refers to an absorbent article generally worn by infants and incontinent persons about the lower torso. The present invention is also applicable to other absorbent articles such as incontinence briefs, incontinence undergarments, absorbent inserts, training pants, diaper holders and liners, and the like.

In one embodiment of the present invention the disposable absorbent article is a disposable diaper. Typically, modern disposable diapers comprise a liquid pervious topsheet a liquid impervious backsheet; an absorbent core which is preferably positioned between at least a portion of the topsheet and the backsheet; side panels; elasticized leg cuffs; an elastic waist feature; and a fastening system. In one embodiment opposing sides of the disposable diaper may be seamed or welded to form a pant. This allows the article to be used as a pull-on type diaper, such as a training pant. Additional illustrative, but non-limiting, information on construction, assembly, and the various components of disposable diapers may be found in U.S. Pat. No. 3,860,003 to Buell; U.S. Pat. No. 5,151,092 to Buell; U.S. Pat. No. 5,221,274 to Buell; U.S. Pat. No. 5,554,145 to Roe et al. on Sep. 10, 1996; U.S. Pat. No. 5,569,234 to Buell et al.; U.S. Pat. No. 5,580,411 to Nease et al.; U.S. Pat. No. 6,004,306 to Robles et al.; U.S. Pat. No. 5,938,648 to LaVon et al.; U.S. Pat. No. 5,865,823 to Curro; U.S. Pat. No. 5,571,096 to Dobrin et al.; U.S. Pat. No. 5,518,801 to Chappell, et al.; U.S. Pat. 4,573,986 to Minetola et al.; U.S. Pat. No. 3,929,135, to Thompson; U.S. Pat. No. 4,463,045 to Ahr, et al.; U.S. Pat. No. 4,609,518 to Curro et al.; U.S. Pat. No. 4,629,643 to Curro et al.; U.S. Pat. No. 5,037,416 to Allen et al.; U.S. Pat. No. 5,269,775 to Freeland et al.; U.S. Pat. No. 4,610,678 to Weisman et al.; U.S. Pat. No. 4,673,402 to Weisman et al.; U.S. Pat. No. 4,888,231 to Angstadt; U.S. Pat. No. 5,342,338 to Roe; U.S. Pat. No. 5,260,345 to DesMarais et al.; U.S. Pat. No. 5,026,364 to Robertson; U.S. Pat. No. 3,848,594 to Buell; U.S. Pat. No. 4,846,815 to Scripps; U.S. Pat. No. 4,946,527 to Battrell; U.S. Pat. No. 4,963,140 to Robertson et al.; U.S. Pat. No. 4,699,622 to Toussant et al.; U.S. Pat. No. 5,591,152 to Buell et al.; U.S. Pat. No. 4,938,753 to Van Gompel, et al.; U.S. Pat. No. 5,669,897 to LaVon, et al.; U.S. Pat. No. 4,808,178 to Aziz et al.; U.S. Pat. No. 4,909,803 to Aziz et al.: U.S. Pat. No. 4,695,278 to Lawson and U.S. Pat. No. 4,795,454 issued to Dragoo.

In one alternative embodiment of the present invention a portion of the absorbent article, such as part or all of the topsheet, part or all of the barrier leg cuffs and the like, may be optionally coated with a lotion, as is known in the art. Examples of suitable lotions include, but are not limited to, those described in U.S. Pat. No. 5,607,760 to Roe on; U.S. Pat. No. 5,609,587 to Roe; U.S. Pat. No. 5,635,191 to Roe et al.; U.S. Pat. No. 5,643,588 to Roe et al.; and U.S. Pat. No. 5,968,025 to Roe et al.

The wetness indicator may be applied to a substrate via any means of liquid or semi-liquid application as known in the art, including, but not limited to, slot coating, spraying, gravure printing, ink jet printing, and digital printing. Alternatively, the wetness indicator may be a solid or semi-solid material affixed to a substrate via adhesive bonding, chemical bonding or intermolecular force bonding. Multiple indicators may be applied to the same substrate in overlapping or non-overlapping geometries. The solidification process may be accelerated via the use of convective mass transport, if evaporation of a solvent is required, or convective or conductive heat transfer, e.g., cooling via air or chilled rolls, etc.

The wetness indicator composition when present on a substrate preferably provides a signal visible from outside the substrate, while the product is being worn, e.g. visible to the wearer, a caregiver, parent and the like . That is, the wetness indicator compositions are affixed to the substrate at a portion which enables it to be in fluid communication with the liquid, e.g. urine, menses, blood and the like, and allows the change initial color state to its final color state to visible to an observer. For example, color or contrast change, is visible through the substrate and/or the absorbent article, such as, the of backsheet or garment-facing covering of a disposable diaper article, which is also in fluid communication with the liquid, such as urine menses, blood and the like, deposited in the absorbent core of the substrate and/or the absorbent article.

In one optional embodiment of the present invention, the change of the colorant from its initial color state to its final color state is visible within a short time after the wetness indicator composition is contacted with a liquid, e.g. urine, menses, blood and the like. In one alternative preferred embodiment of the present invention, the change of the colorant from its initial color state to its final color state is visible within about 15 minutes, more preferably within about 5 minutes after liquid, such as urine, menses, blood and the like, contacts the wetness indicator composition.

In another optional embodiments of the present invention, the substrate, or absorbent article comprising the substrate may be designed to allow liquid, such as urine, menses, blood, and the like, to contact the wetness indicator composition in certain regions of the substrate, or absorbent article at various loading levels. For example, a disposable diaper may be designed to allow urine to contact the wetness indicator composition located in the crotch region of the product on the first urination, but contact the wetness indicator composition in other regions of the disposable diaper only after the amount of urine in the disposable diaper reaches a predetermined threshold value. For example, the absorbent core of the disposable diaper may have limited ability to distribute urine from a given region of the disposable diaper until it contains sufficient urine to change the colorant in a wetness indicator from its initial color state to its final color state in this region, thereby preventing change of the wetness indicator composition in adjacent regions of the article until the overall urine loading in the disposable diaper increases above a given level. As the total urine loading in the disposable diaper increases, more regions of the disposable diaper will contain sufficient urine to change the colorant in a wetness indicator that may be located in those regions from its initial color state to its final color state.

The wetness indicator compositions may be present on a substrate in any desired pattern or configuration, including, but not limited to, stripes, dots, geometric shapes, irregular shapes, alphanumeric characters, pictorial representation of animals, pictorial representation of inanimate objects, cartoon characters, anthropomorphic images, logos, trademarks and any combination or arrangement thereof. The wetness indicating compositions may be applied in any pattern or in conjunction with permanent graphics, such as, permanent graphics on the outer surfaces of a disposable absorbent article.

In one embodiment of the present invention the wetness indicator compositions, when present on a substrate is typically employed at levels which are effective at providing signal visible, preferably from about 1 g per square meter (gsm) to about 100 gsm, more preferably from about 5 gsm to about 60 gsm, and even more preferably still from about 10 gsm to about 30 gsm. However, it is to be understood that the amount of wetness indicator present on a substrate will depend upon many factors, such as but not limited to, substrate type (e.g., thick, thin, opacity, bulky, dense, other physical properties etc.), substrate material, intended use of the substrate (e.g. disposable diaper, panty liner, bandage etc.), method used for applying the wetness indicator compositions, desired intensity of signal in either dry or after contacting liquid, desired pattern or configuration of wetness indicator composition on substrate, and combinations thereof.

Additional information on incorporation of wetness indicating compositions in and/or on substrates and/or disposable absorbent articles can be found disclosed in U.S. Pat. No. 4,022,211 issued, on May 10, 1977, to Timmons; U.S. Pat. No. 6,297,42, issued on Oct. 2, 2001, to Olson; U.S. Pat. No. 6,307,119 issued on Oct. 23, 2001 to Cammarota; and U.S. patent applications Ser. Nos. 20,020,007,162A1 entitled "Absorbent articles having wetness indicating graphics incorporating a training zone," filed on Aug. 13 2001, published Jan. 17, 2002, in the name of Cammarota; and 20,010,053,898A1 entitled "Absorbent articles having wetness indicating graphics providing an interactive training aid" filed on Jul. 24 2001, published Dec. 20, 2001, in the name of Olson; and WO 00/76438 published on Dec. 21, 2000, and assigned to Kimberly-Clark Worldwide Inc., and WO 00/76443 published on Dec. 21, 2000, and assigned to Kimberly-Clark Worldwide Inc.

EXAMPLES

Example 1

| | % by Weight | |
|---|---|---|
| Component | A | B |
| First Binding agent[1] | 48.8 | 58.8 |
| HLB Modifier[2] | 16.0 | 16.0 |
| Viscosity Modifier[3] | 4.0 | 4.0 |
| Stabilizer[4] | 9.0 | 5.0 |
| Second Binding agent[5] | 4.0 | 4.0 |
| Colorant[6] | 0.2 | 0.2 |
| Surfactant[7] | 18.0 | 12.0 |
| Ratio of First Binding agent to Second binding agent | 12.2:1 | 14.7:1 |

[1]Partial Ester of Rosin, (Sylvatac RE 99–70 from Arizona Chemical, Jacksonville, FL)
[2]W835 Microcrystalline Wax from Crompton, Petrolia, PA
[3]Ethylene-Vinyl Acetate copolymer (Elvax 240 from DuPont, Wilmington, DE)
[4]Stearyl Phosphate, (MAP180 from Uniqema, Wilmington, DE)
[5]Second binding agent is a mixture of two cationic materials. The mixture is 75%, or 3.0 % by weight of composition Dimethyl(2-ethylhexylhydrogenated tallowalkyl)ammonium methyl sulfate, (HTL8(W)-MS) from Akzo Incorporated, Chicago, IL) and 25%, or 1.0% by weight of composition of Cocoalkylmethyl[ethoxylated(15)] ammonium chloride (Ethoquad C/25) from Akzo Incorporated, Chicago, IL).
[6]Bromocresol Green, Free Acid from Curtiss Labs, Bensalem, PA
[7]$C_{20}$–$C_{40}$ Pareth-10 (Performathox 450 from New Phase Incorporated, Sugar Land, TX)

Examples 1A and 1B may be made by mixing the HLB modifier and viscosity modifier and heating the mixture at 120° C. for approximately 5 hours or until completely melted. Reduce the heat on this HLB/Viscosity modifier premix to 100° C. and maintain mixing. In another clean, glass container, mix the first binding agent, stabilizer, and the surfactant. Heat and stir this mixture at 90° C. until completely melted. Add in the HLB/Viscosity modifier premix to the mixture of first binding agent/stabilizer/surfactant and heat and mix at 90° C. Add to this mixture the second binding agent and mix until the temperature reaches 90° C. Finally, add to this mixture the colorant and mix for approximately 1 hour at 90° C. until the mixture is clear, transparent and light orange in color.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A wetness indicating composition comprising:
   (a) a colorant, said colorant having an initial color state, said initial color state being associated with a first state of said composition and a final color state, said final color state being associated with a second state of said composition; and
   (b) a matrix comprising a mixture of a first binding agent and a second binding agent; wherein said first binding agent immobilizes said colorant when it is in its said initial color state and said second binding agent immobilizes said colorant when it is in its said final color state; and wherein said second binding agent is selected from the group consisting of cationic clay materials, quaternary ammonium compounds, ethoxylated quaternary ammonium compounds, quaternized silicone compounds, cationic guars, cationic exchange resins, anionic exchange resins, polyacrylic acid polymers, organic acids, and combinations thereof.

2. The wetness indicating composition of claim 1 wherein the ratio of said first binding agent to said second binding agent is from about 2:1 to about 40:1.

3. The wetness indicating composition of claim 1 wherein said colorant is a pH indicator.

4. The wetness indicating composition of claim 1 wherein said colorant is selected from the group consisting of bromocresol green, bromocresol purple, bromophenol blue, m-cresol purple, cresol red, chlorophenol red, bromothymol blue, bromopyrogallol red, bromoxylenol blue, acridine, acridine orange, and combinations thereof.

5. The wetness indicating composition of claim 1 wherein said first binding agent immobilizes said colorant, by one or more forces selected from the group consisting essentially of adhesion, hydrogen bonding, polar covalent bonding, Van der Waal's forces, ionic forces, dipole-dipole force, London dispersion forces and combinations thereof.

6. The wetness indicating composition of claim 1 wherein said second binding agent immobilizes said colorant by covalent bonding, ionic bonding, and combinations thereof.

7. The wetness indicating composition of claim 1 wherein said first binding agent is selected from the group consisting of rosin eaters, polymerized rosins, styrenated terpenes, polyterpene resins, terpene phenolics, and combinations thereof.

8. The wetness indicating composition of claim 7 wherein said first binding agent is a rosin ester.

9. The wetness indicating composition of claim 1 further comprises one or more selected from the group consisting of:
  (c) a stabilizer;
  (d) a surfactant;
  (e) a structural adjunct; and
  (f) combinations of (c), (d) and (e).

10. The wetness indicating composition of claim 9 wherein said stabilizer (c) is selected from the group consisting of monostearyl phosphate, citrate esters, alcohol ethoxycarboxylates, glycolate esters, lactate esters, fatty acids, ether carboxylic acids, fatty acid methyl esters, sulfate esters, fruit acids, inorganic acids, monoethanolamine, diethanolamine, triethanolamine, dipropylenetriamine, diisopropyl amine, 1,3-bis(methylamine)-cyclohexane, 1,3-Pentanediamine, sodium hydroxide, magnesium hydroxide and combinations thereof.

11. The wetness indicating composition of claim 9 wherein said surfactant (d), is selected from the group consisting of nonionic surfactants, anionic surfactants, cationic surfactants and combinations thereof.

12. The wetness indicating composition of claim 9 wherein said structural adjunct (e), is selected from the group consisting of HLB modifiers, viscosity modifiers, hardening agents, and combinations thereof.

13. The wetness indicating composition of claim 1 wherein said first state of said composition is a first pH value, said second state of said composition is a second pH value, wherein said second pH value is different than said first pH value and is substantially the same as the pH of urine.

14. A disposable absorbent article comprising a wetness indicating composition according to claim 1, wherein said composition is affixed to a structural component of said disposable absorbent article.

15. A disposable absorbent article comprising a wetness indicating composition affixed to a structural component of said article, said wetness indicating composition comprising:
  (a) a colorant, said colorant having an initial color state, said initial color state being associated with a first state of said composition and a final color state, said final color state being associated with a second state of said composition; and
  (b) a matrix comprising a mixture of a first binding agent and a second binding agent; wherein said first binding agent immobilizes said colorant when it is in its said initial color state and said second binding agent immobilizes said colorant when it is in its said final color state and the ratio of said first binding agent to said second binding agent is from about 2:1 to about 40:1; and
  wherein said second binding agent is selected from the group consisting of cationic clay materials, quaternary ammonium compounds, ethoxylated quaternary ammonium compounds, quaternized silicone compounds, cationic guars, cationic exchange resins, anionic exchange resins, polyacrylic acid polymers, organic acids, and combinations thereof.

16. The disposable absorbent article of claim 15 wherein said wetness indicating composition is affixed to said article in one or more patterns selected from the group consisting of stripes, dots, geometric shapes, irregular shapes, alphanumeric characters, anthropomorphic images, pictorial representation of animals, pictorial representation of inanimate objects, cartoon characters, logos, trademarks and combinations thereof.

17. The disposable absorbent article of claim 15 wherein said colorant is selected from the group consisting of bromocresol green, bromocresol purple, bromophenol blue, m-cresol purple, cresol red, chlorophenol red, bromothymol blue, bromopyrogallol red, bromoxylenol blue, acridine, acridine orange, and combinations thereof.

18. The disposable absorbent article of claim 15 further comprises a matrix additive, said matrix additive is selected from the group consisting of:
  (c) a stabilizer;
  (d) a surfactant;
  (e) a structural adjunct; and
  (f) mixtures of (c), (d) and (e).

19. The disposable absorbent article of claim 15 wherein said first binding agent is a rosin ester.

* * * * *

UNITED STATES PATENT AND TRADEMARK OFFICE
CERTIFICATE OF CORRECTION

PATENT NO. : 6,904,865 B2
DATED : June 14, 2005
INVENTOR(S) : Thomas James Klofta et al.

It is certified that error appears in the above-identified patent and that said Letters Patent is hereby corrected as shown below:

Column 3,
Line 14, delete "." after "eye,".
Line 60, delete "pyrazoline" and insert -- pyrazolone --.

Column 15,
Line 30, delete "eaters," and insert -- esters, --.

Signed and Sealed this

Seventh Day of February, 2006

JON W. DUDAS
*Director of the United States Patent and Trademark Office*